(12) United States Patent
Smith et al.

(10) Patent No.: US 7,972,367 B2
(45) Date of Patent: *Jul. 5, 2011

(54) DEVICE AND METHOD USING INTEGRATED NEURONAL CELLS AND AN ELECTRONIC DEVICE

(75) Inventors: Douglas H. Smith, Boothwyn, PA (US); Bryan Pfister, Newtown, PA (US); David F. Meaney, Media, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 372 days.

This patent is subject to a terminal disclaimer.

(21) Appl. No.: 12/194,693

(22) Filed: Aug. 20, 2008

(65) Prior Publication Data

US 2008/0305087 A1 Dec. 11, 2008

Related U.S. Application Data

(63) Continuation of application No. 10/496,476, filed as application No. PCT/US02/38670 on Dec. 4, 2002, now Pat. No. 7,429,267.

(60) Provisional application No. 60/386,982, filed on Jun. 6, 2002, provisional application No. 60/336,975, filed on Dec. 4, 2001.

(51) Int. Cl.
*A61N 1/00* (2006.01)
(52) U.S. Cl. ........................................................... 607/1
(58) Field of Classification Search .................. 607/1, 2, 607/46, 48, 45
See application file for complete search history.

(56) References Cited

U.S. PATENT DOCUMENTS

| | | | |
|---|---|---|---|
| 4,306,561 | A | 12/1981 | de Medinaceli |
| 4,774,967 | A | 10/1988 | Zanakis et al. |
| 4,878,913 | A | 11/1989 | Aebischer et al. |
| 5,328,843 | A | 7/1994 | Fukuda et al. |
| 6,264,944 | B1 | 7/2001 | Smith |
| 6,365,153 | B2 | 4/2002 | Smith |

FOREIGN PATENT DOCUMENTS

WO WO 01/12207 2/2001

OTHER PUBLICATIONS

Smith et al., 2001, BED—vol. 50, 2001 Bioengineering Conference, ASME 2001 (Jun. 27-Jul. 1), pp. 413-414.
Smith et al., 2001, Tissue Engineering 7: 131-139.

*Primary Examiner* — Scott M Getzow
(74) *Attorney, Agent, or Firm* — Riverside Law LLP

(57) ABSTRACT

The present invention provides a device of integrated neuronal cells interfaced with an electronic device and a method of producing the same.

15 Claims, 1 Drawing Sheet

3-15 CENTIMETER DISTANCE

US 7,972,367 B2

DEVICE AND METHOD USING INTEGRATED NEURONAL CELLS AND AN ELECTRONIC DEVICE

CROSS-REFERENCE TO RELATED APPLICATIONS

This application is a continuation of U.S. application Ser. No. 10/496,476, filed Nov. 17, 2004, now allowed, which is a National Stage application of PCT/US02/38670, filed Dec. 4, 2002, which in turn claims the benefit under 35 U.S.C. §119 of U.S. provisional applications Ser. Nos. 60/336,975, filed on Dec. 4, 2001 and 60/386,982, filed on Jun. 6, 2002, whose contents are incorporated herein by reference in their entireties.

STATEMENT REGARDING FEDERALLY SPONSORED RESEARCH OR DEVELOPMENT

This invention is supported in part by funds obtained from the U.S. Government (National Institutes of Health Grant Number AG012527), and the U.S. Government therefore has certain rights in the invention.

BACKGROUND OF THE INVENTION

The human brain is an exceedingly complex processing system, which integrates continual streams of incoming sensory input data with stored memories, uses the input data and memories in complex decision processes at both conscious and unconscious levels, and on the basis of these processes generates observable behaviors by activation of its motor or movement control pathways and the muscles which these innervate.

In the United States, approximately 12,000 people each year suffer some form of spinal cord injury (SCI), with over 275,000 people chronically paralyzed from SCI. There are two general types of SCI: complete and incomplete lesions. Complete lesions leave the patient with no motor, sensory, or autonomic function below the level of the lesion. Transection of the spinal cord is the most obvious cause of a complete lesion. The level of the injury in the spinal cord determines exactly what function will be lost, as the spinal nerves that exit the cord below this are absolutely unable to transmit signals to or from the brain. Incomplete lesions can take a variety of forms, and depending on the nature of the trauma, a range of motor and sensory abilities may be present.

Non-traumatic pathologies such as stroke and Parkinson's disease are also often characterized by a patient's inability to successfully translate a desire into the appropriate motions of the relevant limbs. Central nervous system pathologies are often responsible for varying levels of paralysis, which cause immense suffering in the affected population.

Rehabilitation efforts for these patients usually focus on teaching means for using still-functioning limbs to carry out desired tasks, while trying, when possible, to recover some function in the affected limbs. In addition, a range of technologically advanced and expensive devices have been built and tested on patients with limited success. Amongst these are muscle-stimulation devices, which include electrodes that are mounted on a patient's muscles in a paralyzed limb. In response to a command, the electrodes drive current into the muscles causing the contraction thereof. The resultant motion of the limb is typically rough, and the unnatural stimulation protocols often leave the patient's muscles tired, even after performing only a small number of tasks.

U.S. Pat. Nos. 5,178,161; 5,314,495 and 4,632,116 provide the use of microelectrodes to interface between control electronics and human nerves.

U.S. Pat. No. 4,649,936 discloses an electrode cuff for placement around a nerve trunk, for generation of unidirectional propagating action potentials.

U.S. Pat. No. 4,019,518 provides methods for using an electrical stimulation system to selectively stimulate portions of the body.

U.S. Pat. Nos. 5,776,171; 5,954,758 and 6,026,328 disclose methods and devices for stimulating muscles of limbs of the body, so as to achieve motion and control of the limbs in patients with central nervous system disabilities. Limb motions in each limb are commanded by external means and communicated via radio waves to an apparatus implanted in the limb. Actual motion of the limb is monitored and compared to the commanded motion with the goal of attaining real-time control of the limb.

U.S. Pat. No. 5,748,845 provides a device for controlling limbs of patients with central nervous system disabilities. The activity of a healthy muscle is sensed, analyzed, and used to determine input parameters to a control system of the device. Both external mechanical apparatus and direct electrical stimulation of muscle tissue are described as means for inducing movement of the disabled limb.

Other methods and devices for sensing muscular contractions and for applying muscular stimulation are provided by U.S. Pat. Nos. 6,091,977; 6,104,960; 6,086,525; 4,926,865; 4,392,496 and 6,146,335.

U.S. Pat. No. 6,119,516 discloses a biofeedback system, optionally including a piezoelectric element, which measures the motions of joints in the body. U.S. Pat. No. 5,069,680 provides the use of a piezoelectric crystal as a muscle activity sensor. U.S. Pat. Nos. 4,602,624 and 5,505,201 disclose techniques for making implantable electrodes. U.S. Patent Application No. 20020161415 further provides a plurality of electrodes, which are adapted to be placed in a vicinity of a motor nerve that innervates the skeletal muscle.

Despite these advances there remains a need for a means to communicate with the regions of the brain via an external interface which is plastically adaptive, sensitive, and responsive to the subtleties of nerve transmission.

SUMMARY OF THE INVENTION

The present invention provides integrated neuronal cells, which may be mechanically elongated to lengths of greater than one centimeter, interfaced with an electron device. Said neuronal cells are capable of transmitting electrical signals to and receiving electrical signals from an electronic device and may comprise nerve bundles.

The present invention further provides a method of producing integrated neuronal cells interfaced with an electronic device. The method provides placing a first neuronal cell on an electronic device which is adjacent to a membrane which contains a second neuronal cell and allowing the cells to integrate. In a preferred embodiment, the integrated neuronal cells are elongated using a mechanical device.

These and other aspects of the present invention are set forth in more detail in the following description of the invention.

DETAILED DESCRIPTION OF THE INVENTION

The primary functional constituents of the spinal cord are myelinated axons and neurons. Signals travel from brain to body and back via these axons which synapse to spinal neurons communicating with the targeted body region. At present, electronic devices to interface with this complex system of communication include wires or devices placed in proximity with the region of the brain of interest. However, only very crude signals can be recorded from or transferred to the brain in this fashion.

Figure 1:
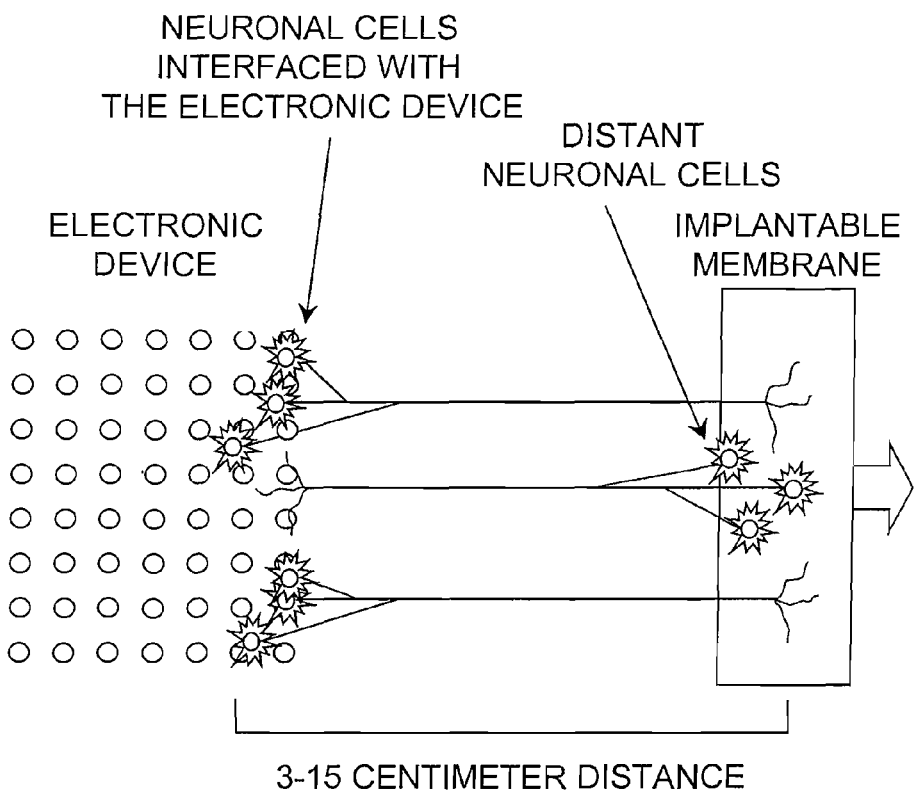
FIG. 1 is a schematic representation of integrated elongated neuronal cells attached to an implantable membrane and an electronic device.

An improved device has now been found to bridge electronic devices with biological processes. The device is integrated neuronal cells physically attached to or grown onto an implantable membrane and an electronic device (FIG. 1). The electronic device is used to send signals to or receive signals from the brain and/or other peripheral regions of the body. The advantage of the current device is that it comprises a living, spontaneously adaptive system of neuronal cells and an electronic device. Furthermore, when the neuronal cells have been mechanically elongated they allow for the electronic device to be located either outside of the body or implanted at an internal location which can be tolerated by the patient.

One aspect of the invention provides a method of producing integrated neuronal cells interfaced with an electronic device. The method comprises placing a first population of neuronal cells on an electronic device which is adjacent to a membrane containing a second population of neuronal cells. The membrane may be any material, however a biologically absorbable material is preferable as it is more compatible for transplantation into tissue. The two populations of neurons are allowed to mature and integrate among each other, including growth of axons across the border between the electronic device and membrane. In a preferred embodiment, the electronic device and membrane are progressively separated using, for example, a micro-stepper motor system (see, e. g., U.S. Pat. No. 6,264,944, herein incorporated in its entirety), resulting in two populations of cell bodies connected together by elongated fascicular axon tracts.

Figure 2A:
FIGS. 2A and 2B show integrated elongated neurons attached to a multi-electrode array.
Figure 2B:
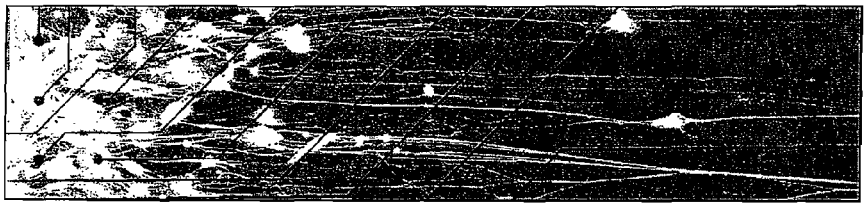

Using the method of the invention, rat dorsal root ganglion were attached to a membrane and a multi-electrode array electronic device (FIGS. 2A and 2B). It was found that dorsal root ganglion cells could be elongated to lengths of over three to five centimeters at an average rate of six millimeters per day. The maximal rate obtained was eight mm/day sustained for 24 hours with no evidence of axonal breakage or damage. Modified elongation devices may be engineered to produce neuronal cells elongated to lengths of 15 cm.

Short axon segments were found to be very sensitive to the rate of stretch-growth. If axons were allowed to grow at a slow to moderate rate for several days, the axons could be ramped to higher stretch rates without axonal damage. Axons that were grown for one day at a rate of 1 mm/day and then ramped to 6 mm/day showed a significant amount of axonal breakage after 2 days. However, if the axons were allowed to elongate for a period of 3 days at 1 mm/day and then ramped to 6 mm/day, there was no evidence of axonal breakage.

Adult and embryonic DRG cells were elongated. Adult DRG cells took longer to initiate regenerative growth in culture following dissection and dissociation.

Approximately one additional week in culture (compared to embryonic cells) was required for adult DRGs to grow sufficient axons across the elongation interface. Adult DRG cells also were constrained to a slower rate of elongation; a maximum of 1 mm/day for 7 days was attainable.

Immunocytochemistry of the elongated fascicular axon tracts revealed a normal cytoskeleton containing phosphorylated neurofilament, tau and β-tubulin protein expression. The results indicated that the heavy neurofilament (NF-H, 200 kDa) was present throughout the entire elongated axon length. All axons studied showed the same result over several studies and at each rate and length. Antibodies to the phosphorylated NF-H (SMI-32) and a non-specific NF-200 antibody had significant reactivity in all elongated axons. β-tubulin was also identified using the SMI-61 and SMI-62 antibodies for unassembled and assembled-tubulin, respectively. Moreover, tau protein expression, which is reportedly the slowest of the transported cytoskeletal proteins, was found in significant amounts throughout each and every elongated axon. Similar results were found for adult DRG elongated axons.

Transmission electron micrographs were prepared for the cross-sections of both stretch-induced elongation and growth cone induced growth of DRG axons. Microtubules were counted and cross-sectional areas were measured. The results showed that stretch induced axon elongation leads to a hypertrophy of axonal caliber. On average, the axon cross-sectional area increased by 30% and the median cross sectional area increased by almost 50%.

In a preferred embodiment of the present invention, neuronal cells are derived from any cell that is a neuronal cell (e. g., cortical neurons or dorsal root ganglion neurons) or is capable of differentiating into a neuronal cell (e. g., stem cell) and can function in the central nervous system or peripheral nervous system. Moreover, these cells may be derived from cell lines or other mammalian sources such as donors or volunteers. Furthermore, the neuronal cells may be singular, integrated neuronal cells or a plurality of integrated neuronal cells (i.e., an integrated nerve bundle) interfaced with an electronic device. When the electronic device is interfaced with a nerve bundle, a signal may be transmitted from an external control module to stimulate one, some, or all of the axons in the nerve bundle, thereby causing, for example, contraction of a muscle. Preferably, the control module contains circuitry which regulates the magnitude, frequency, and/or duration of the electric signal transmitted by the electronic device.

In another preferred embodiment the electronic device interfaced with a neuronal cell or nerve bundle comprises a multi-electrode array, as exemplified herein, or any electronic device capable of transmitting and receiving electrical signals including, but not limited to, an electrode, microchip or sensor/actuator.

It is contemplated that the device of the invention will be useful as a source of transplant material for patients with spinal cord injury as well as other nerve lesions such as those derived from a neurodegenerative disease. The device may also be used to restore communications of a severed limb or organ of the peripheral nervous system with the central nervous system. Methods for transplantation of the cells of the device of the invention are well-known to those of skill in the art of cell transplantation. Suitable transplant material may be evaluated by using well-known electrophysiological and fluorescence techniques to demonstrate that digital signals can be sent from the electronic device to the attached neurons and stimulate an action potential to be received by the distant neurons. Likewise, distant neurons grown on the transplantable membrane may be stimulated to demonstrate that a signal can be received by the electronic device.

Transplanted cells are oriented such that the distant neuron is implanted in the brain or at or near a site of nerve damage and the electronic device is exteriorized. In this manner, the signals generated by the brain cells or viable cells at or near the site of nerve damage may be exteriorized. Signals received from the brain, for example, may be used to control external prostheses, such as an assist robot or an artificial arm; computers or computer displays; or functional electrical stimulation of muscles of paralyzed individuals for the restoration or enhancement of movement.

As one of skill in the art can appreciate, the device of the present invention would permit a signal to be sent from the brain to the electronic device to allow a subject to control a device such as a prosthesis or robot. That is, the subject would transmit a signal, the impulse would be transmitted by an implanted neuronal cell interfaced with an electronic device, an external control module would measure and convert the impulse received by the electronic device from the brain, the external control module would then transmit a signal to a second electronic device interfaced with a prosthesis or robot which undertakes the activity that is imagined or intended. Known methods for measuring brain electrical impulses are described, for example, in U.S. Pat. No. 4,862,359. Methods of controlling robotics or prostheses are disclosed in U.S. Pat. No. 6,171,239 and Amirikian, et al. ((1999) Can. J. Exp. Psych. 53: 21-34.

Furthermore, the device of the present invention would permit a signal to be sent to the brain from the electronic device. For example, a phototransistor microprocessor array may serve as the electronic device attached to the integrated neuronal cells. The distant neuronal cells attached to an implantable membrane are then transplanted into the lateral geniculate nucleus (LGN) region of the thalamus, which functions as a junction box for visual signals. Elongation of the neuronal cells allows the phototransistor microprocessor array to be exteriorized to receive light impulses outside the cranium. These impulses are then sent deep into the brain by the distant neurons. Behavioral tests and electrophysiologic analysis are performed to evaluate the function of the implant.

The invention is described in greater detail by the following non-limiting examples.

EXAMPLE 1

Embryonic Dorsal Root Ganglion Cell Isolation

Dorsal root ganglia (DRG) were isolated from E15 (EO is the day after mating) rat embryos. Dissected ganglia were held in Lebovitz L-15 medium during the isolation. Dissociated cultures were treated with 0.25% trypsin (Sigma-Aldrich, St. Louis, Mo.) in a cell dissociation buffer (INVITROGEN™, Carlsbad, Calif.) and incubated at 37° C. for 45 minutes. Trypsin activity was stopped with the addition of L-15 medium+20% fetal bovine serum (FBS; Hyclone, Logan, Utah) and cells were centrifuged at 1000 rpm for five minutes. After discarding the supernatant, the cell pellet was resuspended in 2 mL of complete medium consisting of Neural Basal Medium (INVITROGEN™, Carlsbad, Calif.) supplemented with B27 (INVITROGEN™, Carlsbad, Calif.), 1% FBS (Hyclone, Logan, Utah), 1 mM L-Glutamine (INVITROGEN™, Carlsbad, Calif.), and 2.5 g/L glucose. The DRGs were then triturated ten times with a fire-polished pipette. Cells were counted and plated on a collagen-or laminin-coated surface at a density of 1-2×10$^6$ cells per mL.

Whole DRGs were plated immediately following isolation in complete media. Plating of whole DRGs allows for very high plating densities and leads to much larger axon fascicles during mechanical elongation. The whole DRGs may be "softened" by a one minute trypsin treatment followed by trypsin inactivation with L-15+20% FBS. Pelleted ganglia are resuspended in complete media gently using a Pasteur pipette and immediately plated.

EXAMPLE 2

Adult Dorsal Root Ganglion Cell Isolation

The adult DRGs were dissected from adult Sprague-Dawley rats of at least eight weeks of age (Scott (1977) J. Neurobiol. 8 (5): 417-27). Briefly, the spinal column was removed from the brain-cervical junction to below L1. Attached tissue and the spinous processes were removed using a pair of roungers. The column was cut with a pair of tough iris scissors starting at the cervical end, cutting through the dorsal roof bone (staying centered as not to damage the ganglia). The column was then separated lengthwise in half by carefully cutting through the cord and ventral side of the column. The spinal cord and menengies along the inner spinal column were removed using fine forceps and the DRGS were pulled from the foramen. Using small spring scissors, the nerves on both sides of the DRG were cut. Two incisions were made on each side of ganglia and placed into bovine serum albumin (BSA) coated tubes containing L-15 medium during the isolation.

Adult DRGs are myelinated and must be dissociated to separate the neurons from the surrounding tissues and supporting cells. Dissected DRGs were treated in 0.25% collegenase-P (Boehringer Mannheim, Germany) in Neural Basal medium for 1.5 hours. All the DRGs and tissues were pelleted and resuspended in 0.25% trypsin in cell dissociation buffer for an additional 1.5 hours. Trypsin activity was stopped with 20% FBS in Neural Basal medium and the cells were centrifuged. The pellet was resuspended in complete medium and mechanically separated using a fire-polished Pasteur pipette until the DRGs were completely dissociated.

An almost pure suspension of DRGs was obtained by passing the dissociated product through a BSA gradient. A two-layer BSA gradient (5% and 10%) was prepared by adding 5 mL of a 5% BSA solution in a 15 mL centrifuge tube. Using a Pasteur pipette, the second layer was added below the 5% BSA by slowly pipetting the 10% BSA solution with the Pasteur pipette tip at the bottom of the tube. The 5% BSA floats on top the 10% BSA. The dissociated DRG suspension was carefully placed on top of each gradient by adding it drop by drop along the side of the tube. The gradient tubes were centrifuged at 100×g for seven minutes. Most of the DRG cells and non-neuronal cells pelleted while the myelin and Schwann cells were found in the upper fractions of the gradient. Pellets were resuspended in 5 mL of complete media, and carefully placed on a second BSA gradient prepared as described. The gradients were centrifuged at approximately 90×g for no more than five minutes. This centrifugation step removed most of the smaller non-neuronal cells from the larger DRG cells. The pellets were resuspended in complete medium, counted and plated.

EXAMPLE 3

Axon Elongation Device

Dorsal root ganglion cell axons were grown by tension induced elongation (Smith, et al. (2001) Tissue Eng. 7: 131-138). The device consistently separates two adjoining substrates on which neural cells are cultured. The adjoining substrates were placed such that axons growing in culture could grow across the interface between the two substrates easily. The bottom substrate, an electronic device, was placed in the bottom of the elongation device on which a stationary population of neurons was cultured. An overlapping ACLAR® substrate (Honeywell, Berkshire, UK), i. e., the towing substrate, was placed on top of the electronic device substrate and served as the moving population of cells. Once the neurons and their axons matured and synapsed across the bottom and towing substrate interface, the two substrates were separated using a micro-stepper motor system (Smith, et al. (2001) Tissue Eng. 7: 131-138; U.S. Pat. No. 6,264,944). The result was two populations of cell bodies connected together via elongated fascicular axon tracts.

EXAMPLE 4

Elongation Device Preparation, Plating, and Maintenance

Cell culture plates, the ACLAR® surface, and the electronic device were coated with collagen prior to DRG plating. After ACLAR® was cut into desired sizes, it was washed with laboratory soap and rinsed well. ACLAR® was then treated in 1 M NaOH for 24-48 hours, rinsed well in sterile water, then bathed in 100% ethanol for 10 minutes. The ACLAR® was then allowed to dry on a sterile rack in a cell culture hood. The ACLAR® substrate was attached to the elongation device framework using medical grade RTV silicone (NuSil, Carpinteria, Calif.). During curing, RTV silicone releases acetic acid, which can be lethal to cells, therefore the silicone was allowed a minimum of three days to completely cure prior to plating cells. Twenty-four hours after assembly, the ACLAR® surface was treated with 10 µg/mL poly-L-lysine (PLL) for 4 hours. The PLL solution was removed and the ACLAR® was allowed to dry for one hour and the surface was subsequently rinsed three times with sterile water. After the silicone has completely cured the ACLARO surface was coated with type 1 rat-tail collagen (Becton Dickinson, Franklin Lakes, N.J.). Collagen was spread over the surface (10-20 µL per cm$^2$) and polymerized by exposure to ammonia vapors for two minutes. The collagen was then allowed to dry completely in a cell culture hood before plating cells. The electronic device was sterilized and coated with collagen in a similar manner.

The hydrophobic collagen surface provides that cells can be plated in any desired arrangement by applying the cell suspension in a puddle and allowing the cells to attach for about 2-4 hours before the chamber is flooded with media. Embryonic, dissociated cells cultures were plated at a density of 1-2×10$^6$ cell per mL of which 500 µL was plated along the adjoining substrate interface of the elongation device. Whole embryonic DRGs were plated from 6-8 pups in 500 µL of complete medium along the substrate interface of the elongation device. Dissociated DRG cells from one adult rat were resuspended in 1 mL of complete medium of which 500 µL was plated on each of two elongation devices.

After cell attachment, the elongation device chamber was flooded with complete medium with mitotic inhibitors, 10 µM FdU and 10 µM Uridine. The media was changed every two to three days and the mitotic inhibitors applied once a week. On day five, the elongation device was turned on and left undisturbed without changing the medium. For long-term experiments, the media was changed once a week.

EXAMPLE 5

Axon Elongation Scheme

Five days after plating, the DRG cells were elongated. Elongation was controlled by displacement of the towing membrane. Since stretch induced growth was initially strain limited, elongation began at a slow rate and was increased to the desired growth rate. Stretch rate was programmed into the motion control device by choosing a displacement, and a resting time in a step-wise fashion. For example, 1 mm/day was programmed as 1 µm displacements every 86.4 seconds.

Elongation started at 1 mm/day (1 µm every 86.4 seconds) for the first 24 hours. The elongation rate was then increased by 1 mm/day every 6 to 12 hours until the maximum elongation rate was achieved. In the case of a maximal rate of 8 mm/day, the ramping was slower and at 12 to 24 hour intervals to allow the axons to increase in length.

EXAMPLE 6

Tissue Fixation, Immunocytochemisty and Electron Microscopy

For immunocytochemistry, the elongated tissue was fixed with 4% paraformaldehyde for 60 minutes. Following three rinses in phosphate-buffered saline (PBS), elongated axons were blocked with 4% Normal Goat Serum (NGS) in PBS at room temperature for 60 minutes. The primary and secondary antibodies were applied in 4% NGS, 0.1% Triton X in PBS for 60 minutes each. Primary antibodies targeted to the 200 kDa neurofilament fragment where NF200, diluted 1:400 (Sigma-Aldrich, St. Louis, Mo.), and SMI-32, diluted 1:400 (Sternberger Monoclonals, Lutherville, Md.). Antibodies to β-tubulin where SMI-61 & 62, diluted 1:400 (Sternberger Monoclonals, Lutherville, Md.) and the antibody to Tau was diluted 1:400 (Dako, Denmark). Fluorescent secondary antibodies were used according to manufacturer's instructions (Molecular Probes, Eugene, Oreg.).

For transmission electron microscopy, elongated axons were fixed in 4% paraformaldehyde, 2% glutaraldehyde, in 0.1 M sodium cacodylate buffer, overnight at 4° C. To prevent any damage to the axons during their removal from the elongation device, the tissue was supported in 2% agar. Melted agar was allowed to cool to approximately 45° C. then gently pipetted over the tissue. The agar was allowed to cool and harden at 2° C. With a #11 scalpel, the substrates were carefully cut loose and the tissue removed. The tissue was then washed in the same buffer and post-fixed in 1% osmium tetroxide for 1 hour at 4° C. After another buffer wash, the sample was dehydrated in a graded ethanol series before infiltration and embedding in epoxy resin (EMbed-812; Electron Microscopy Sciences, Fort Washington, Pa.). Thin sections were cut at 800 Å and placed on formvar-coated grids. After staining with uranyl acetate and lead citrate, sections were examined with a JEOL 100CX transmission electron microscope.

For scanning electron microscopy, elongated axons were fixed in 4% paraformaldehyde, 2% glutaraldehyde, in 0.1 M sodium cacodylate buffer, overnight at 4° C. The sample was rinsed and post-fixed in 1% osmium tetroxide for 30 minutes. After another buffer wash, the sample was dehydrated in a graded ethanol series followed by a drying step of two applications of Hexamethyldisilazane (HMDS, Electron Microscopy Sciences, Fort Washington, Pa.) of ten minutes each.

What is claimed is:

1. A method of treating a spinal cord injury or a nerve lesion using a device comprising first and second isolated neuronal cells, the method comprising transplanting the second isolated neuronal cell of the device at or near a site of nerve damage, wherein the device comprises an electronic device, wherein the first isolated neuronal cell is interfaced with the electronic device wherein the first isolated neuronal cell is integrated to the second isolated neuronal cell via elongated axons greater than 1 cm in length.

2. The method of claim 1, wherein the elongated axons are greater than 3 cm in length.

3. The method of claim 1, wherein the neuronal cells transmit an electrical signal to the electronic device.

4. The method of claim 1, wherein the neuronal cells receive an electrical signal from the electronic device.

5. The method of claim 1, wherein the integrated neuronal cells comprise fascicular axon tracts.

6. The method of claim 1, wherein the second isolated neuronal cell is attached to an implantable membrane.

7. The method of claim 1, wherein the electronic device is a multi-electrode array.

8. The method of claim 1, wherein the first isolated neuronal cell comprises a first population of isolated neuronal cells.

9. The method of claim 1, wherein the second isolated neuronal cell comprises a second population of isolated neuronal cells.

10. The method of claim 8, wherein the second isolated neuronal cell comprises a second population of isolated neuronal cells.

11. The method of claim 1, further comprising an external control module operably connected to the electronic device.

12. The method of claim 11, further comprising a second electronic device operably connected to the external control module.

13. The method of claim 12, wherein the second electronic device is interfaced with one of a prosthesis, a robot, a computer, a computer display or a muscle.

14. The method of claim 1, wherein the isolated neuronal cell is transplanted into the lateral geniculate nucleus region of the thalamus and wherein said electronic device is a phototransistor microprocessor array.

15. The method of claim 1, wherein the nerve lesion is associated with a neurodegenerative disease.

* * * * *